US009410119B2

(12) United States Patent
Nakanishi et al.

(10) Patent No.: US 9,410,119 B2
(45) Date of Patent: Aug. 9, 2016

(54) CELL CULTURE DEVICE, CELL CULTURE SYSTEM, AND CELL CULTURE METHOD

(71) Applicant: ARKRAY, Inc., Kyoto-shi (JP)

(72) Inventors: Naoyuki Nakanishi, Kyoto (JP); Yuichiro Noda, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 0 days.

(21) Appl. No.: 14/226,197

(22) Filed: Mar. 26, 2014

(65) Prior Publication Data

US 2014/0295541 A1 Oct. 2, 2014

(30) Foreign Application Priority Data

Mar. 28, 2013 (JP) .................................. 2013-069154
Feb. 24, 2014 (JP) .................................. 2014-033156

(51) Int. Cl.
| C12M 1/00 | (2006.01) |
| C12M 3/00 | (2006.01) |
| C12N 5/071 | (2010.01) |
| C12M 1/26 | (2006.01) |

(52) U.S. Cl.
CPC ............. *C12N 5/0602* (2013.01); *C12M 21/08* (2013.01); *C12M 23/02* (2013.01); *C12M 23/26* (2013.01); *C12M 23/40* (2013.01); *C12M 23/44* (2013.01); *C12M 29/26* (2013.01); *C12M 33/12* (2013.01); *C12M 41/14* (2013.01)

(58) Field of Classification Search
CPC .................................................. C12N 5/0602
USPC ....................................................... 435/289.1
See application file for complete search history.

(56) References Cited

U.S. PATENT DOCUMENTS

| 5,846,828 A * | 12/1998 | Peterson ................. A61F 2/062 435/284.1 |
| 6,090,062 A * | 7/2000 | Sood et al. ......................... 604/9 |
| 2005/0042745 A1* | 2/2005 | Tsuzuki et al. ............. 435/295.3 |
| 2010/0093066 A1* | 4/2010 | Taylor et al. ................ 435/284.1 |
| 2011/0130310 A1* | 6/2011 | Schober et al. ................. 506/39 |

FOREIGN PATENT DOCUMENTS

| JP | 4330436 B2 | 9/2009 |
| WO | WO-02/26034 A2 | 4/2002 |
| WO | WO-2011/042755 A2 | 4/2011 |

OTHER PUBLICATIONS

Caicedo, H.H., Multiphysics simulation of a microfluidic perfusion chamber for brain splice physiology, May 13, 2010, Biomed Microdevices, 12:761-767.*

* cited by examiner

*Primary Examiner* — Kevin Joyner
*Assistant Examiner* — Holly Mull
(74) *Attorney, Agent, or Firm* — Fox Rothschild LLP

(57) ABSTRACT

To provide a cell culture device, a cell culture system and a cell culture method capable of suppressing fluctuations in pressure in a culture fluid, and suppressing gas bubbles from flowing into a cell culture section. A cell culture device including: a cell culture section that cultures cells; a storage section that stores a culture fluid; flow paths that connect the cell culture section and the storage section; a fluid delivery device that is provided at the flow paths and that delivers the culture fluid from the storage section to the cell culture section; a pressure equalizing unit that is provided at the flow paths and that suppresses fluctuations in pressure imparted to the culture fluid delivered to the cell culture section; and a pressurization unit that is provided at the flow path at a flow outlet side of the cell culture section and that applies a specific pressure to the culture fluid.

7 Claims, 13 Drawing Sheets

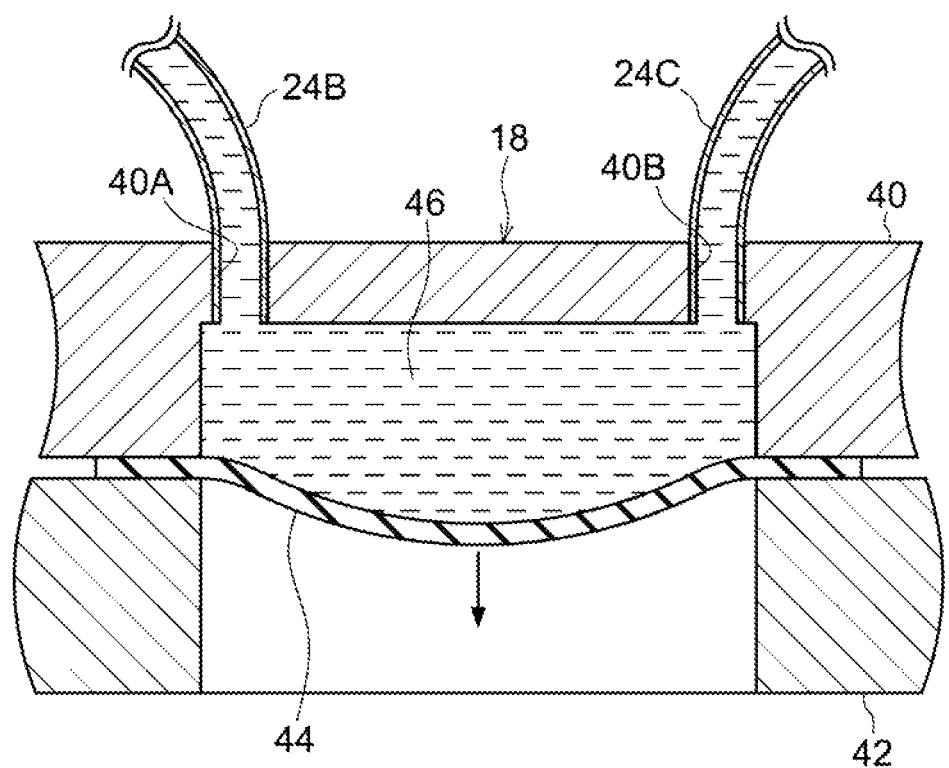

CELL CULTURE DEVICE, CELL CULTURE SYSTEM, AND CELL CULTURE METHOD

CROSS-REFERENCE TO RELATED APPLICATION

This application is based upon and claims the benefit of priority of the prior Japanese Patent Application No. 2013-069154, filed on Mar. 28, 2013, and the Japanese Patent Application No. 2014-033156, filed on Feb. 24, 2014, the entire contents of which are incorporated herein by reference.

FIELD

The present invention relates to a cell culture device, a cell culture system and a cell culture method.

BACKGROUND

Cell culture devices are known in which cells are cultured while culture fluid is being delivered and circulated by a pump (fluid delivery device). Moreover Japanese Patent No. 4330436 describes a cell culture device provided with a gas chamber (air damper), and in which pulsations of a pump (fluid delivery device) are absorbed.

SUMMARY

Cell culture devices that deliver a culture fluid during cell culture need to deliver the culture fluid over a long period of time. As a result, a high capacity syringe pump is required in cases in which a constant capacity pump such as a syringe pump is used to deliver fluid. Due to their bulkiness, such high capacity syringe pumps cannot be placed on a microscope stage, making it difficult to perform regular observation of the cell culture state. Moreover, large devices are less portable, so compact tubing pumps or the like are suited to culture fluid delivery.

An issue arises in that, due to their structure, pulsations in tubing pumps are unavoidable, so the flow rate of the culture fluid cannot be made constant. The present inventor has confirmed through repeated experimentation that cell death can be avoided by suppressing pulsations and maintaining the culture fluid flow rate within a constant range.

Even when a gas chamber is provided, sometimes pulsations of the pump (fluid delivery device) cannot be sufficiently absorbed, and the pressure of the culture fluid fluctuates and variation in the flow rate cannot be suppressed. Namely, if the volume of the gas chamber fluctuates due to a temperature change, its resilience as an air damper fluctuates and it becomes difficult to maintain a constant pulsation suppression function. Moreover, air inside the gas chamber expands if the temperature increases and there is a risk of gas bubbles becoming mixed in with the culture fluid. If the capacity of the gas chamber is increased in order to avoid the above issue, then the device becomes bulky. A compact cell culture device capable of suppressing pump pulsations is therefore desired.

Due to reasons such as pH regulation and cytotoxicity, culture fluid used in cell culture generally includes a carbonate component buffering system. The occurrence of gas bubbles, such as carbon dioxide gas bubbles, in the culture fluid due to factors such as temperature change becomes more likely as a result. Since these gas bubbles are a cause of cell death, the occurrence of gas bubbles needs to be suppressed. The present inventor performed the above investigation and identified the need for a cell culture device that is capable of suppressing pump pulsations and is capable of reducing gas bubble occurrence, and has arrived at the present invention.

In consideration of the above circumstances, an object of one aspect of the present invention is to provide a cell culture device, a cell culture system and a cell culture method that are capable of suppressing fluctuations in pressure in culture fluid and also capable of suppressing influx of gas bubbles into a cell culture section.

Solution to Problem

A cell culture device according to a first aspect of the present invention includes: a cell culture section that cultures cells; a storage section that stores a culture fluid; a flow path that connects the cell culture section and the storage section; a fluid delivery device that is provided at the flow path and that delivers the culture fluid from the storage section to the cell culture section; a pressure equalizing unit that is provided at the flow path and that suppresses fluctuations in pressure imparted to the culture fluid delivered to the cell culture section; and a pressurization unit that is provided at the flow path at a flow outlet side of the cell culture section and that applies a specific pressure to the culture fluid.

In the above aspect of invention, the culture fluid is delivered from the storage section to the cell culture section through the flow path by the fluid delivery device. The pressure equalizing unit provided at the flow path suppresses fluctuations in pressure imparted to the culture fluid delivered to the cell culture section. This thereby enables pulsations in the culture fluid to be to be constrained, and variations in the flow rate to be suppressed.

Moreover, the pressurization unit is provided at the flow path at the flow outlet side of the cell culture section. Gas within the culture fluid is suppressed from forming gas bubbles by the pressurization unit applying a specific pressure to the culture fluid, enabling death of cells caused by air bubbles to be avoided. As a result, for example, occurrence of gas bubbles can be suppressed even if the temperature of the culture fluid changes. Moreover, applying pressure to the culture fluid enables gas bubbles to be dissolved in the culture fluid. Furthermore, the pulsation can be further reduced when pressure is applied to the culture fluid, compared to cases disposed only with the pressure equalizing unit, without the pressurization unit.

Moreover, even when the flow rate of the culture fluid delivered by the fluid delivery device is changed, pulsations are suppressed by the pressure equalizing unit and the pressurizing unit, thereby enabling minor adjustments to the culture fluid flow rate to be made without sudden fluctuations in the culture fluid flow rate. This thereby enables delivery of the culture fluid at a flow rate that is appropriate for culture of the cells. As described above, providing a pressure equalizing unit, and further disposing a pressurizing unit to the flow path at the flow outlet side of the cell culture section, enables a practical cell culture device to be obtained.

A cell culture device according to a second aspect of the present invention is the first aspect, in which the pressure equalizing unit includes: a fluid chamber charged with the culture fluid; a flow inlet and a flow outlet that are formed to the fluid chamber and are connected to the flow path; and a flexible membrane that configures a portion of an inner wall of the fluid chamber, and that flexes according to pressure fluctuations in the fluid chamber.

In the above aspect of invention, the flow chamber volume increases and decreases due to flexing of the flexible membrane to match pulsations, enabling fluctuations in flow chamber pressure to be reduced. Moreover, in cases in which a gas chamber is employed to suppress pressure fluctuations, the volume of the gas chamber fluctuates corresponding to temperature changes, and the culture fluid flow rate is unstable. However, in the pressure equalizing unit of the present invention, due to employing the flexible membrane, the flow chamber volume does not increase or decrease even when the temperature changes, enabling the culture fluid flow rate to be stabilized.

A cell culture device according to a third aspect of the present invention is the second aspect, in which: the flow inlet and the flow outlet are formed at opposing end portions of the fluid chamber; and the fluid chamber is formed so as to gradually widen on progression from the end portions toward a center portion.

In the above aspect of invention, incorporation of gas bubbles when the flow chamber is being charged with the culture fluid is suppressed, enabling death of cells caused by gas bubbles to be avoided.

A cell culture device according to a fourth aspect of the present invention is the cell culture device according to the third aspect, in which the fluid chamber has a rhombus shape with rounded corners in plan view.

The above aspect of invention enables suppression of gas bubbles entering and residing in the corner portions of the rhombus shape.

A cell culture device according to a fifth aspect of the present invention is the cell culture device according to the first aspect, in which the pressurization unit includes a pressurization portion that is connected to the flow path, and that has a smaller cross-sectional area than the flow path; and a resilient membrane that configures a portion of a wall face of the pressurization portion, and that undergoes resilient deformation due to pressure of the culture fluid that has flowed into the pressurization portion.

The above aspect of invention enables pressure to be applied to the culture fluid merely by making the culture fluid flow into the pressurizing portion. When the culture fluid reaches a specific pressure or greater at this time, gas bubbles are dissolved in the culture fluid, enabling death of cells to be avoided. Moreover, for example, in cases in which a narrow width tube body is connected and pressure is applied, there is a possibility that cells become stuck in the tube body and the flow path pressure fluctuates. In contrast thereto, by configuring the portion of the pressurization portion wall face with the flexible membrane, the resilient membrane is capable of undergoing resilient deformation to widen the flow path width, thereby enabling suppression of cells becoming stuck.

A cell culture device according to a sixth aspect of the present invention is the invention according to the first aspect, in which a gas bubble removal part that removes gas bubbles is provided at the flow path at flow inlet side of the cell culture section.

The above aspect of invention enables gas bubbles in the culture fluid to be removed by the gas bubble removal part prior to the culture fluid flowing into the cell culture section, thereby enabling avoidance of gas bubbles flowing into the cell culture section and killing the cells therein.

A cell culture device according to a seventh aspect of the present invention according to the first aspect, in which plural pressure equalizing unit are provided.

The above aspect of invention enables greater suppression of fluctuations in pressure in culture fluid compared to a case in which only one pressure equalizing unit is provided. Moreover, the culture fluid flow rate can be more finely set.

A cell culture system according to a eighth aspect of the present invention includes the cell culture device of the first aspect, and a thermostatic container that houses the cell culture device.

The above aspect of invention enables cells to be cultured at a temperature appropriate for culture of the cells by housing the entire cell culture device in the thermostatic container. Moreover, occurrence of gas bubbles due to changes in ambient temperature can be suppressed. Note that an observation means, such as a microscope, may be included to the cell culture system in order to observe the cells grafted to the cell culture section.

A cell culture method according to a ninth aspect employs the cell culture device of the first aspect to culture cells, and the cell culture method includes: a process of adding cells to at least one of the cell culture section, the storage section, or the pressure equalizing unit; and a process of circulating the culture fluid within the flow path using the fluid delivery device while pressurizing the culture fluid within the flow path using the pressurization unit.

In the above aspect of invention, cells are added in the cell addition process to at least one of the cell culture section, the storage section, or the pressure equalizing unit. There is no particular constraint to the added cells, and they may be, for example, pluripotent cells. By adding the cells, secretions secreted by the cells flow into the culture fluid and flow into the cell culture section, enabling promotion of cell culture therein. Moreover, the culture fluid is circulated by the circulation process, enabling the culture fluid containing the secretions to be repeatedly delivered to the cell culture portion.

Advantageous Effects of Invention

Due to the configuration described above, the aspects of present invention enables provision of a cell culture device, a cell culture system and a cell culture method capable of suppressing fluctuations in pressure in culture fluid, and suppressing flow of gas bubbles into a cell culture section.

BRIEF DESCRIPTION OF DRAWINGS

FIG. 3 is cross-section view viewed from a front face illustrating the pressure equalizing mechanism according to the first exemplary embodiment when a culture fluid is pulsating.

DESCRIPTION OF EMBODIMENTS

First Exemplary Embodiment

Explanation follows regarding a cell culture system 100 provided with a cell culture device 10 according to a first exemplary embodiment of the present invention, with reference to the drawings. The cell culture system 100 according to the present exemplary embodiment is mainly employed in the culture of pluripotent cells, but is not limited thereto, and may also be employed as a device for culture of other cells. Herein, pluripotent cells refers to cells that are capable of differentiating into plural types of cells. For example, pluripotent cells include but are not limited to: embryonic stem cells (ES cells), germline stem cells (GS cells), embryonic germ cells (EG cells), induced pluripotent stem cells (iPS cells), pluripotent cells (Muse cells) derived from cultured fibroblasts or bone marrow stem cells and adult stem cells. Moreover, pluripotent cells may be derived from various kinds of organisms. Pluripotent cells derived from a mammal, including a human, are preferable, and pluripotent cells derived from a mouse or pluripotent cells derived from a primate are more preferable. Pluripotent cells derived from a human are particularly preferable.

Of the types of pluripotent cell, embryonic stem cells (ES cells) and induced pluripotent stem cells (iPS cells) in particular are expected to be employed in regenerative medicine in the near future. Embryonic stem cells (ES cells) used here refers to stem cells that are established from an inner cell mass of an early stage embryo (such as a blastocyst) of a mammal such as a human or a mouse, and that are pluripotent and capable of propagating by self-replication. Induced pluripotent stem cells (iPS cells) used here refers to stem cells that can be generated by introducing specified reprogramming factors into body cells in the form of DNA or a protein. In particular, induced pluripotent stem cells are artificial stem cells deriving from somatic cells that have substantially the same characteristics as ES cells, such as pluripotency and propagation by self-replication.

Figure 1:
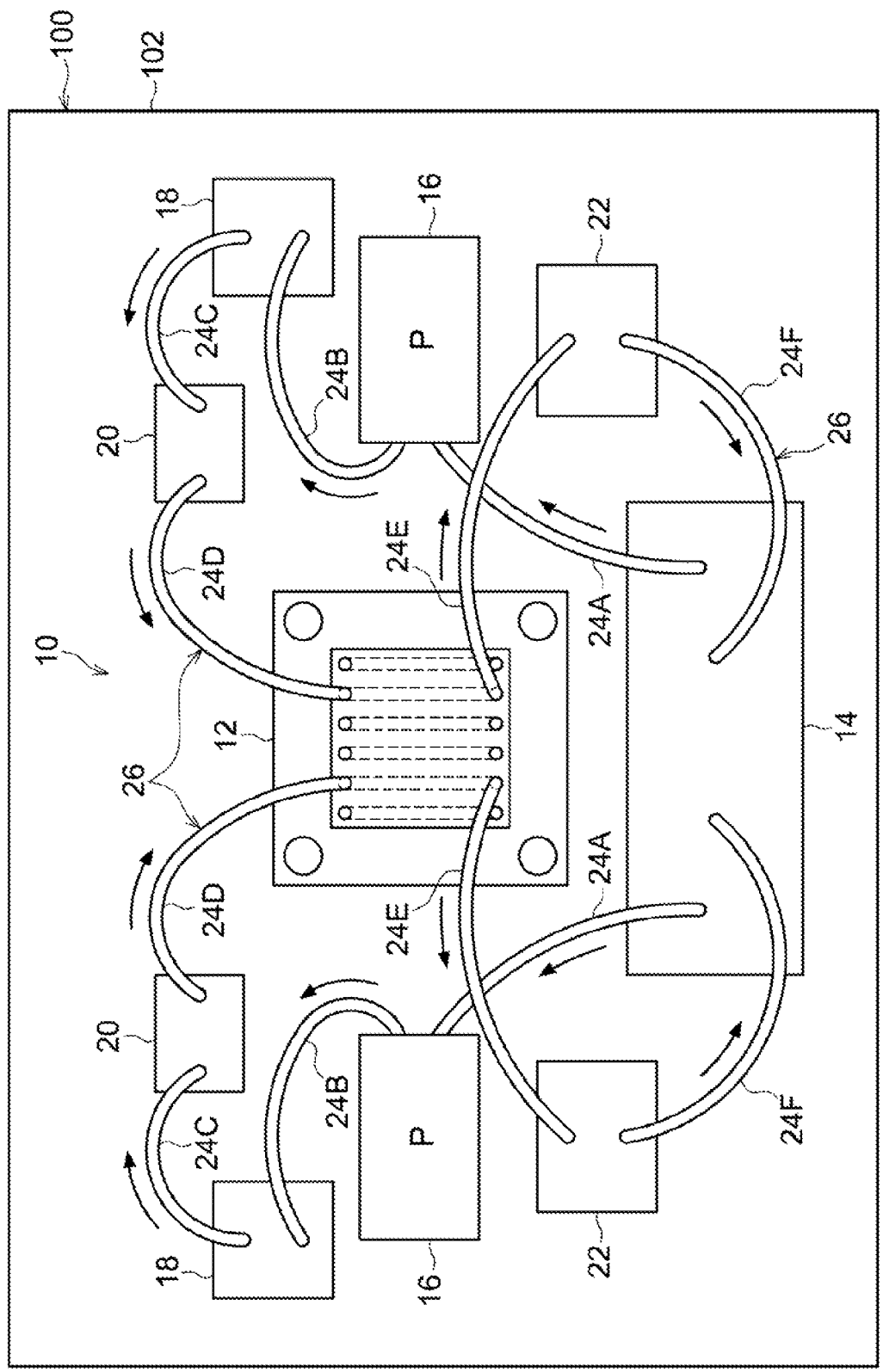
FIG. 1 is a plan view illustrating an overall configuration of a cell culture device according to a first exemplary embodiment.

As illustrated in FIG. 1, the cell culture system 100 according to the present exemplary embodiment is provided with an incubator 102 as a thermostatic container, and the cell culture device 10 is housed inside the incubator 102. The incubator 102, with inside temperature maintained at a specific temperature, needs to be of a size that can house the cell culture device 10. Note that in the present exemplary embodiment, the temperature inside the incubator 102 is maintained at 37 degrees C. in order to perform cell culture at a temperature close to human body temperature, however the temperature is not limited thereto, and a suitable temperature for culture of the cells may be maintained. Moreover, use of a $CO_2$ incubator 102 as the incubator 102 is preferable.

The cell culture device 10 is principally provided with a cell culture section 12, a reservoir (storage section) 14, circulation pumps (fluid delivery device) 16, pressure equalizing mechanisms (pressure equalizing unit) 18, air traps (gas bubble removal part) 20 and pressurization mechanisms (pressurization unit) 22. Tubes 24A to 24F are connected to each section, configuring circulation flow paths 26. Note that in the present exemplary embodiment, of six channels formed to the cell culture section 12, two of the channels are employed for performing culture. As a result, two each are provided of the circulation pumps 16, the pressure equalizing mechanisms 18, the air traps 20 and the pressurization mechanisms 22, however configuration is not limited thereto, and more of the circulation flow paths 26 may be provided corresponding to the number of channels employed. Moreover, plural tubes 24 may be connected to a single circulation pump 16.

Explanation follows regarding each section configuring the cell culture device 10 according to the present exemplary embodiment. The reservoir 14 is provided at the lower side in FIG. 1, and culture fluid is stored inside the reservoir 14. In the present exemplary embodiment, two circulation pumps 16 are connected to a single reservoir 14, however configuration is not limited thereto, and an independent reservoir 14 may be provided for each of the circulation pumps 16.

An appropriate culture fluid corresponding to the cells for culture may be selected for the culture fluid stored in the reservoir 14. For example, a DMEM/F-12 culture fluid supplemented with 0.1 mM of 2-mercaptoethanol, 0.1 mM of non-essential amino acid, 2 mM of L-glutamic acid, 20% KSR and 4 ng/ml of bFGF is used as a culture fluid in order to culture ES cells. DMEM, DMEM/F12, or a DME culture fluid containing 10% to 15% FBS is used as a culture fluid for iPS cell induction. Moreover, commercially available culture fluids (such as culture fluid for mouse ES cell culture, culture fluid for primate ES cell culture, serum-free media and the like) may also be employed.

The circulation pumps 16 serving as the fluid delivery device are connected to the reservoir 14 through the tubes 24A. Various fluid delivery pumps may be used as the circulation pumps 16, but a compact pump with a low flow rate is preferred. In the present exemplary embodiment, peristaltic tubing pumps are used, as an example, however configuration is not limited thereto, and other pumps may also be used. Moreover, in the present exemplary embodiment, the culture fluid is delivered at an average flow rate of 0.75 µl/min or less.

The circulation pumps 16 suck up culture fluid from the reservoir 14 through the tubes 24A and deliver the culture fluid to the tubes 24B. Culture fluid inside the pressure equalizing mechanisms 18, connected to the tubes 24B, is thereby pushed out, and is delivered to the air traps 20 through the tubes 24C. Culture fluid is delivered to the cell culture section 12 through the tubes 24D in a similar way, and delivered onward to the reservoir 14 through the tubes 24E. The culture fluid accordingly circulates around the cell culture device 10 with laminar flow. Note that laminar flow used here refers to flow in which lines of flow in a fluid are parallel to a wall face, and refers to a non-turbulent flow field. It is preferable to have laminar flow, with a flow field in which the flow speed is lower closer to the walls, with the flow speed becoming uniform at a certain distance or more from the wall face.

Figure 2A:
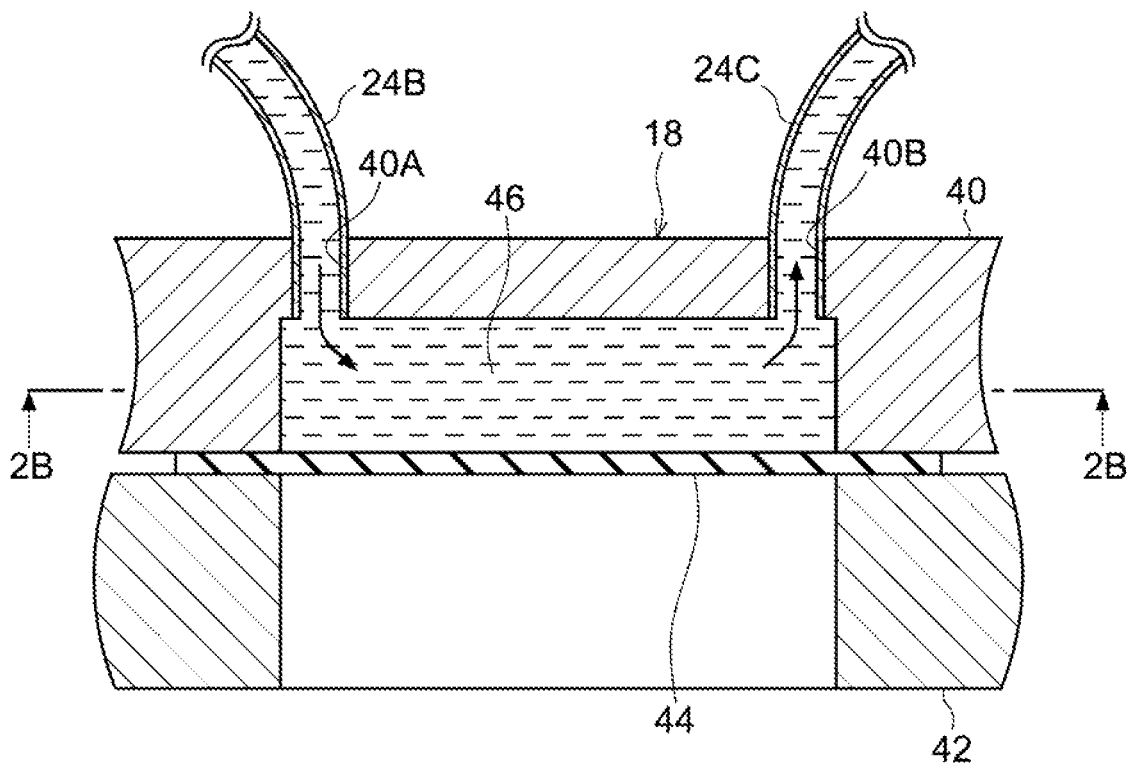
FIG. 2A is a cross-section view viewed from a front face and illustrating a pressure equalizing mechanism according to the first exemplary embodiment.

The pressure equalizing mechanisms 18 serving as pressuring equalizing unit are connected to the circulation pumps 16 through the tubes 24B. As illustrated in FIG. 2A, each pressure equalizing mechanism 18 is principally provided with an upper block 40, a lower block 42 and a flexible membrane 44, the flexible membrane 44 being formed sandwiched between the upper block 40 and the lower block 42. The upper block 40 and lower block 42 are resin blocks. A fluid chamber 46 is formed as a recess in a lower face of the upper block 40.

The fluid chamber 46 is a space charged with the culture fluid, with a flow inlet 40A that passes through an upper face of the upper block 40 formed to one length direction end portion of the fluid chamber 46. The tube 24B is connected to the flow inlet 40A. A flow outlet 40B that passes through the upper face of the upper block 40 is formed to a length direction other end portion of the fluid chamber 46, and is connected to the tube 24C.

Figure 2B:
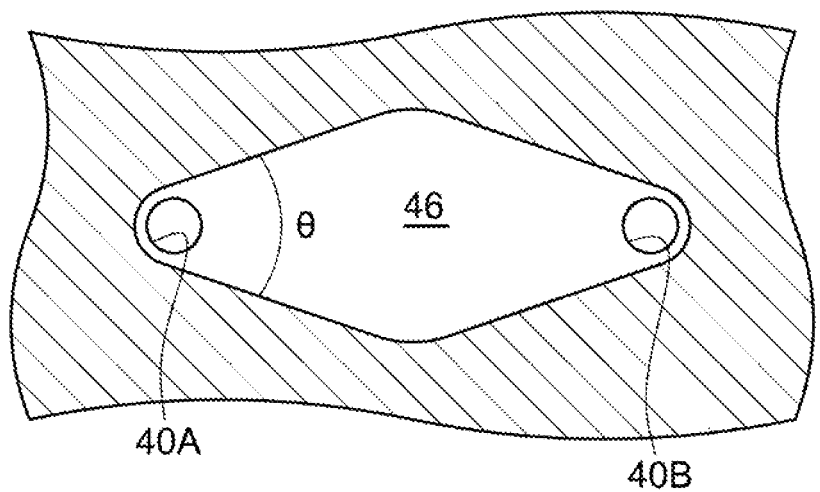
FIG. 2B is a cross-section view taken along line 2B-2B in FIG. 2A.

As illustrated in FIG. 2B, the fluid chamber 46 is formed in a rhombus shape with rounded corners in plan view. This thereby enables suppression of air (gas bubbles) remaining within the fluid chamber 46 when culture fluid flows from the flow inlet 40A to the flow outlet 40B to charge the fluid chamber 46. Moreover, in the present exemplary embodiment, by forming the flow inlet 40A and the flow outlet 40B at positions where the rhombus shape forms acute angles, the width of the fluid chamber 46 gradually widens from the flow inlet 40A toward a center portion of the fluid chamber 46, making gas bubbles less liable to be incorporated when the fluid chamber 46 is charged with the culture fluid. An acute angle θ is preferably from 5 degrees to 90 degrees, more preferably from 8 degrees to 60 degrees, and particularly preferably from 10 degrees to 30 degrees. Note that the corners of the fluid chamber 46 are not necessarily rounded, and the shape does not have to be a rhombus.

As illustrated in FIG. 2A, the flexible membrane 44 is adhered to the lower face of the upper block 40, configuring a portion of an inner wall of the fluid chamber 46. There are no particular limitations to the material for the flexible membrane 44 providing the material is capable of flexing enough to sufficiently change the volume of the fluid chamber 46, and for example a resilient body such as a flexible resin or rubber, or a flexible metal, may be used. Obviously the flexible membrane 44 is formed of a material that does not react with the culture fluid.

When the fluid chamber 46 pressure increases due to, for example, pulsations of the circulation pump 16, the flexible membrane 44 flexes downward and the fluid chamber 46 volume is increased, as illustrated in FIG. 3. The fluid chamber 46 pressure is accordingly lowered, enabling fluctuations in the circulation flow path 26 pressure to be suppressed. Conversely, the flexible membrane 44 flexes upward when the fluid chamber 46 pressure decreases, and the fluid chamber 46 volume decreases. The fluid chamber 46 pressure is accordingly raised, enabling fluctuations in the circulation flow path 26 pressure to be suppressed. In this manner, the pressure can accordingly be equalized by flexing of the flexible membrane 44 corresponding to fluctuations in the fluid chamber 46 pressure.

Note that in the present exemplary embodiment, the flow inlet 40A and the flow outlet 40B are formed at the upper face of the upper block 40 and the culture fluid flows into the fluid chamber 46 from the vertical direction, however configuration is not limited thereto, and the flow inlet 40A and flow outlet 40B may be formed at two side faces of the upper block 40, with the culture fluid flowing into the fluid chamber 46 from the horizontal direction.

Figure 4:
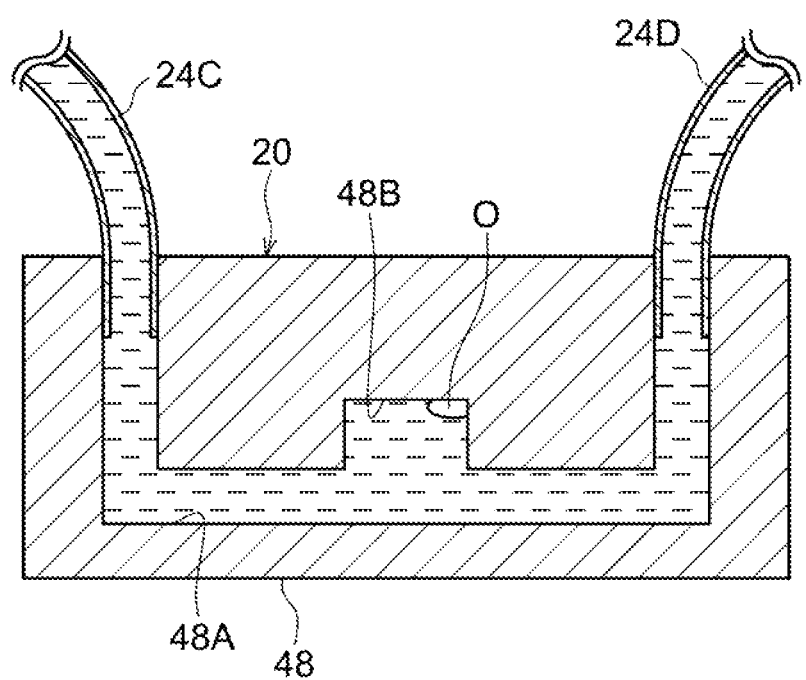
FIG. 4 is enlarged view viewed from a front face illustrating an air trap according to the first exemplary embodiment.

As illustrated in FIG. 1, the air traps 20 serving as the gas bubble removal part are connected to the pressure equalizing mechanisms 18 through the tubes 24C. As illustrated in FIG. 4, a trap main body 48 is provided to the air trap 20, and the tube 24C and the tube 24D are connected to an upper face of the trap main body 48. Moreover, a flow path 48A linking together the tube 24C and the tube 24D is formed inside the trap main body 48.

A trap portion 48B that broadens the width of flow path 48A is formed at a center portion of the flow path 48A. The size of the trap portion 48B is formed with appropriate dimensions corresponding to the culture fluid flow rate and the degree of gas bubble occurrence. As a result, when a gas bubble O occurs in the culture fluid flowing through the flow path 48A, the gas bubble O floats upward while passing through trap portion 48B, and is blocked by a wall face and trapped. The trapped gas bubble O may be vented by opening a vent pipe (omitted from the drawings) formed in the trap main body 48, or may be removed by pressurization with the pressurization mechanism 22.

Figure 5:
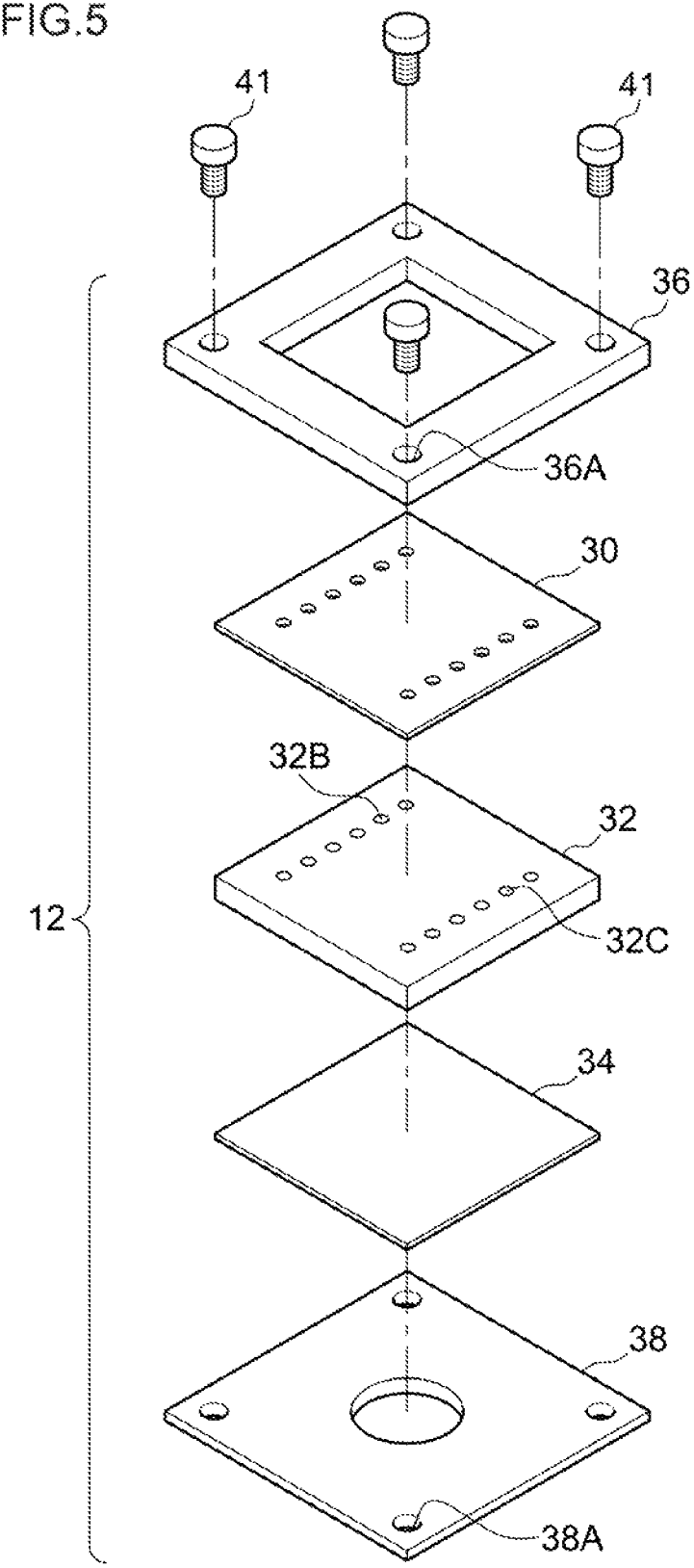
FIG. 5 is an exploded perspective view of a cell culture section according to the first exemplary embodiment.

As illustrated in FIG. 1, the cell culture section 12 is connected to the air traps 20 through the tubes 24D. The cell culture section 12 is a member in which cell culture is performed and is substantially rectangular shaped in plan view. As illustrated in FIG. 5, the cell culture section 12 is provided with a resin plate 30, a polydimethylsiloxane (PDMS) layer 32 and a glass plate 34 formed stacked in that order from the top downward. In a state in which a lower clamp 38 is disposed beneath the glass plate 34, an upper clamp 36 is brought down from above the resin plate 30, and the resin plate 30, the PDMS layer 32, and the glass plate 34 are sandwiched between the upper clamp 36 and the lower clamp 38. In this state, bolts 41 are inserted through and fasten together with bolt holes 36A formed to the upper clamp 36 and bolt holes 38A formed to the lower clamp 38, thereby forming the cell culture section 12.

Six independent slit shaped grooves 32A that form channels are formed to the PDMS layer 32. In the present exemplary embodiment, the grooves 32A are formed, as an example, with width of 0.5 mm, length of 20 mm, and depth of 0.5 mm, but the dimensions are not limited thereto, and the grooves 32A may be formed with other dimensions. A flow inlet 32B and a flow outlet 32C are formed to each of the grooves 32A. Note that in the present exemplary embodiment, the grooves 32A are formed to the PDMS layer 32, however a member made of a different material may be used. For example, a plastic, silicone resin, polymethylmethacrylate, polyurethane, polystyrene or glass may be used.

Figure 6:
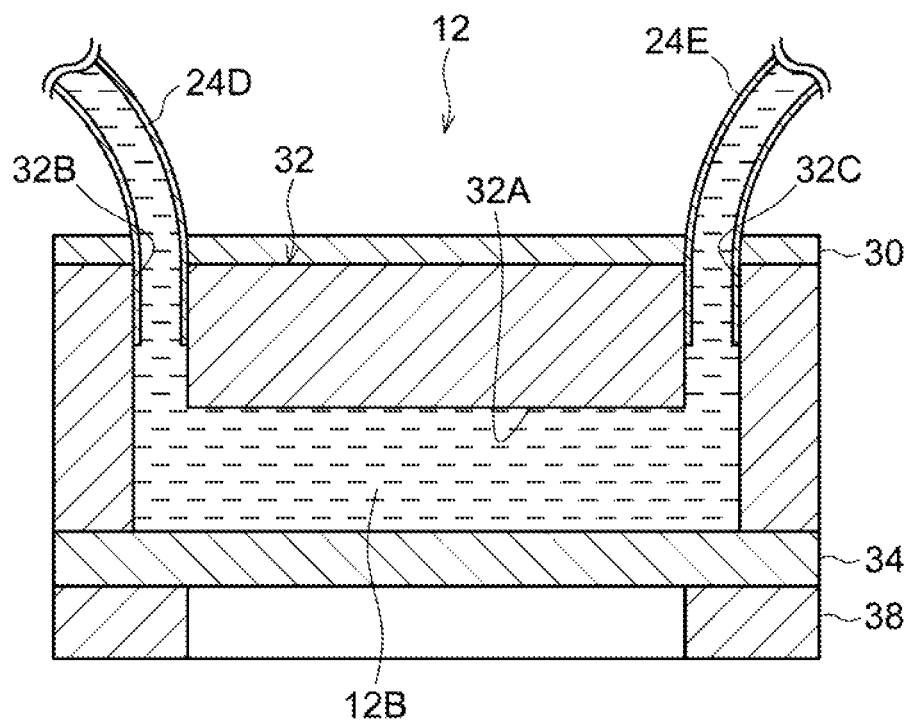
FIG. 6 is a cross-section view of the cell culture section according to the first exemplary embodiment.

As illustrated in FIG. 6, the tubes 24D are connected to the flow inlets 32B, and when culture fluid is delivered from the tubes 24D into the cell culture section 12, the culture fluid arrives at one end portion of a culture chamber 12B formed at a lower portion of the cell culture section 12. Cells are grafted inside the culture chamber 12B, and are cultured by the culture fluid flowing as a laminar flow. The culture fluid that has passed through the culture chamber 12B moves upward from the other end portion of the culture chamber 12B, and flows out from tubes 24E connected to the flow outlets 32C.

Figure 7:
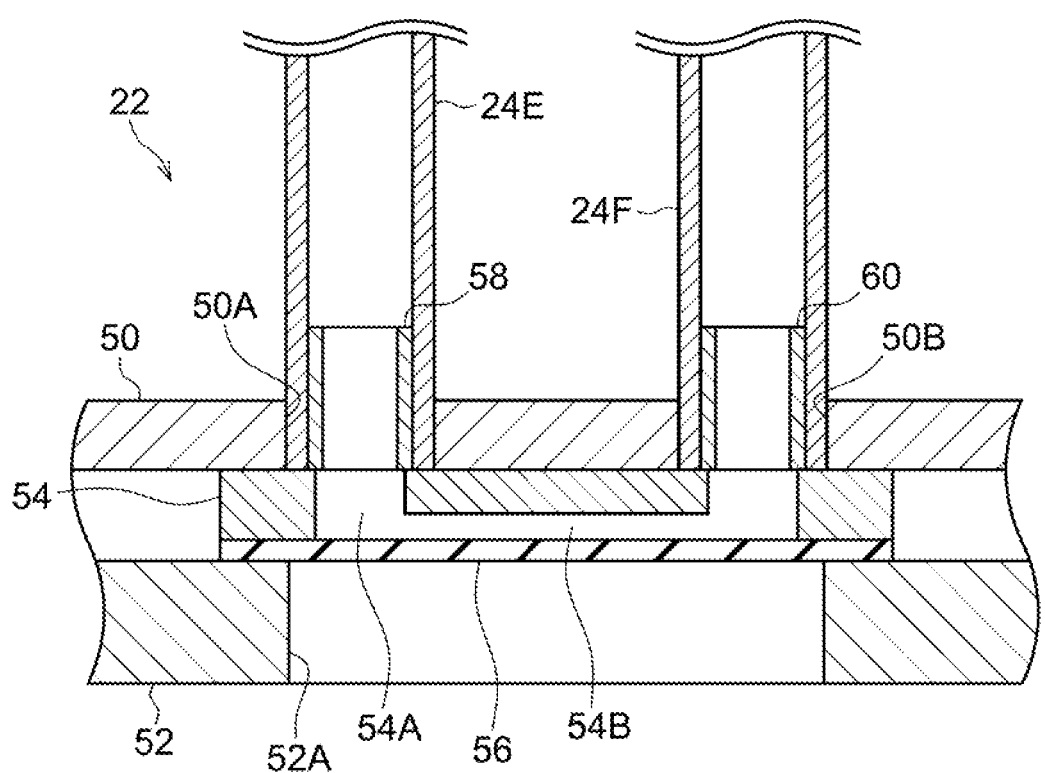
FIG. 7 is an enlarged cross-section view viewed from a front face illustrating a state prior to the culture fluid flowing in a pressurizing mechanism according to the first exemplary embodiment.

As illustrated in FIG. 1, the pressurization mechanisms 22 serving as the pressurization unit are connected to the cell culture section 12 through the tubes 24E. The pressurization mechanisms 22 are mechanisms for pressurizing the culture fluid flowing in the circulation flow paths 26 to a specific pressure. As illustrated in FIG. 7, each pressurization mechanism 22 is principally provided with an upper block 50, a diaphragm base 54, a diaphragm 56 serving as a resilient membrane, and a lower block 52.

The upper block 50 and the lower block 52 are resin blocks. Two through holes 50A, 50B are provided to the upper block 50, and the tubes 24E, 24F are inserted through each of the through holes 50A, 50B respectively. Moreover, inner tubes 58, 60 are respectively inserted inside the tubes 24E, 24F, and the tubes 24E, 24F are respectively interposed between the inner tubes 58, 60 and hole walls of the through holes 50A, 50B.

The lower block 52 is provided beneath the upper block 50 with a separation between lower block 52 and the upper block 50. A through hole 52A is formed at a center portion of the lower block 52. As a result, the diaphragm 56, explained later, does not contact with the lower block 52 when the diaphragm 56 undergoes downward resilient deformation. Note that a recessed portion may also be formed by hollowing out an upper face of the lower block 52.

The diaphragm base 54 is provided between the upper block 50 and the lower block 52. The diaphragm base 54 is a plate shaped resin member formed with a flow path 54A that passes through the diaphragm base 54 at positions corresponding to the through holes 50A, 50B of the upper block 50. The height of a center portion of the diaphragm base 54 is lower than that of a peripheral edge portion.

The diaphragm 56 is attached to a lower face of the diaphragm base 54. The diaphragm 56 is a membrane shaped member capable of resilient deformation. In the present exemplary embodiment, the diaphragm 56 is formed with the same size to that of the diaphragm base 54, however the size is not limited thereto, and the size may be different to that of the diaphragm base 54, providing the size is sufficient to cover the flow path 54A. Furthermore, the diaphragm 56 is adhered to the peripheral edge portion of the diaphragm base 54, and a narrow portion 54B that is narrower in width than the circulation flow paths 26 is formed between the diaphragm 56 and the center portion of the diaphragm base 54.

Figure 8:
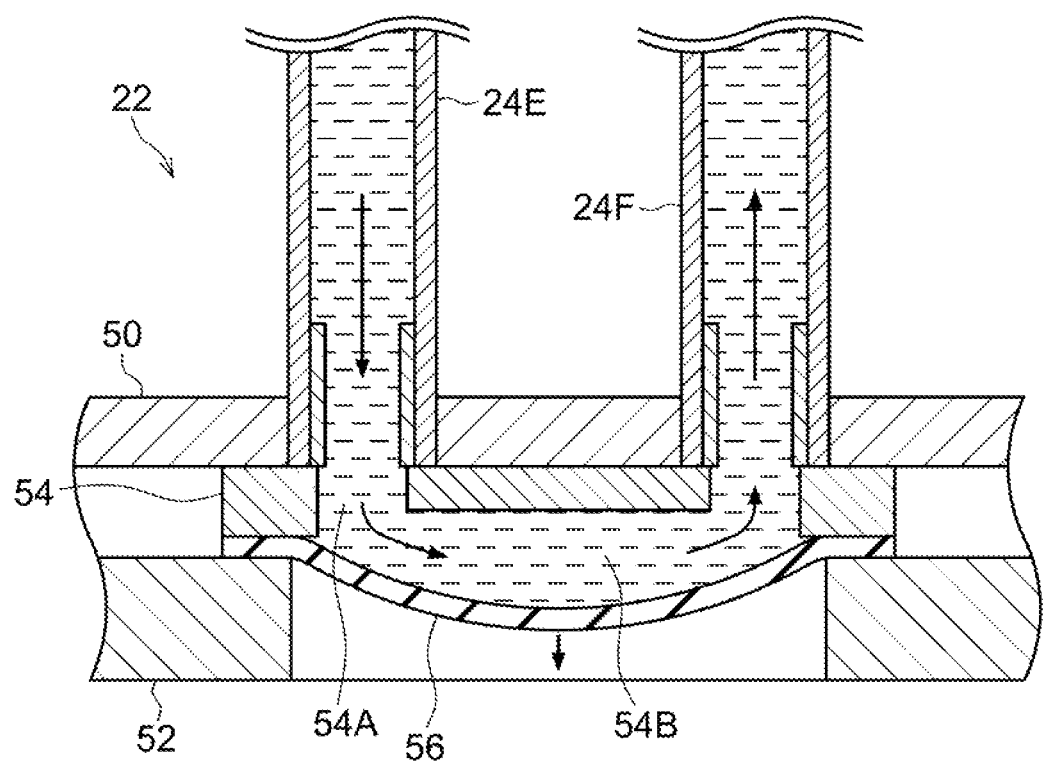
FIG. 8 is an enlarged cross-section view of relevant parts viewed from the front face illustrating a state in which the culture fluid is flowing in the pressurizing mechanism according to the first exemplary embodiment.

When the culture fluid is delivered from the tube 24E to the pressurization mechanism 22, the culture fluid flows from the flow path 54A of the diaphragm base 54 to the narrow portion 54B. As illustrated in FIG. 8, when this occurs the culture fluid is pressurized by the narrow portion 54B and the diaphragm 56 undergoes downward resilient deformation, pushing the narrow portion 54B outward. Restoring force accordingly acts on the resiliently deformed diaphragm 56, applying force in a direction contracting the flow path 54A, thereby pressurizing the culture fluid at the specific pressure. Note that in the present exemplary embodiment, the thickness of the diaphragm 56 and so on are adjusted so as to enable pressurization at 10 kPa, as an example, however the pressure is not limited thereto, and pressurization may be at a pressure of 10 kPa or more.

As illustrated in FIG. 1, the reservoir 14 is connected to the pressurization mechanisms 22 through the tubes 24F. The culture fluid delivered to the reservoir 14 is stored in the reservoir 14, then sucked up by the circulation pumps 16 and circulated around the circulation flow paths 26 until the circulation pumps 16 stop.

Note that in the present exemplary embodiment, the cells are only grafted in the cell culture section 12, however configuration is not limited thereto, and cells may be added to the reservoir 14 or the pressurization mechanisms 22. Sometimes in such cases, secretions secreted by the cells are mixed in with the culture fluid circulated by the circulation pumps 16, enabling promotion of culture of the cells in the cell culture section 12.

Explanation follows regarding the operation of cell culture device 10 according to the present exemplary embodiment. The cell culture device 10 according to the present exemplary embodiment is provided with the pressure equalizing mechanisms 18, thus enabling suppression of fluctuations in the culture fluid pressure due to pulsations of the circulation pumps 16. As a result, the cells do not sustain damage resulting from pressure fluctuations in the culture fluid flowing in the cell culture section 12.

Moreover, the pressurization mechanisms 22, provided to the circulation flow paths 26 on the flow outlets 32C side of the cell culture section 12, pressurize the culture fluid delivered to the cell culture section 12, thus enabling occurrence of gas bubbles in the culture fluid to be suppressed. Furthermore, applying the specific pressure, or greater, enables gas bubbles caught up in the circulation flow path 26 can be dissolved in the culture fluid. Suppressing gas bubbles from flowing into the cell culture section 12 in this way enables death of cells caused by gas bubbles to be avoided.

Moreover, the pressurization mechanisms 22 are formed using the diaphragm 56 that is capable of resilient deformation, enabling steady circulation of the culture fluid without cells in the culture fluid becoming stuck, even when the flow path 54A is narrowed Furthermore, in the cell culture device 10 according to the present exemplary embodiment, providing both the pressure equalizing mechanisms 18 and the pressurization mechanisms 22 enables a synergistic effect to be obtained. Namely, even when pressure fluctuations cannot be sufficiently suppressed by the pressure equalizing mechanisms 18 alone, pressurization of the culture fluid by the pressurization mechanisms 22 enables pressure fluctuations to be suppressed, and also enables occurrence of gas bubbles in the culture fluid to be suppressed.

Moreover, the culture fluid flow rate required in the cell culture device 10 according to the present exemplary embodiment is a low flow rate of 0.75 µl/min or less, enabling the overall size of the device to be made more compact. This thereby, for example, enables the whole device to be taken out from the incubator 102 and carried to a microscope to observe the culture chamber 12B of the cell culture section 12.

Moreover, just changing the flow rate settings of the circulation pumps 16 greatly affects pulsations when the culture fluid is delivered at a low flow rate, which might have potentially prevented fine adjustments from being performed to the flow rate. However, fluctuations in the flow rate are suppressed by providing the pressurization mechanisms 22, enabling fine adjustments to the flow rate. By enabling fine adjustments to be made, culture conditions can be reproduced.

Test Example

The following tests were performed in order to confirm the advantageous effects of the cell culture device 10 according to the present exemplary embodiment.

Test 1: Using the cell culture device 10 according to the present exemplary embodiment, the flow rate of culture fluid delivered to the cell culture section 12 was measured using a micro flow meter, as illustrated in FIG. 10. Moreover, for a cell culture device of a Comparative Example in which the pressure equalizing mechanisms 18 and the pressurization mechanisms 22 have been removed from the cell culture device 10, the flow rate of culture fluid delivered to the cell culture section 12 was measured using a micro flow meter, as illustrated in FIG. 9.

Test 2: Using the cell culture device 10 according to the present exemplary embodiment, the flow rate of culture fluid delivered to the cell culture section 12 was set at 0.3 µl/min, 0.5 µl/min and 0.7 µl/min, and for each case the number of iPS cells grafted to the culture chamber 12B was counted using a microscope and entered into Table 1 on the first day and the third day after starting cell culture. Moreover, the same test was performed using the cell culture device of the Comparative Example described above. Note that the average flow rate of the culture fluid in the cell culture device of the Comparative Example was set at 0.5 μl/min. In all the tests, culture was performed inside a $CO_2$ incubator, and a $1.0 \times 10^5$ cells/ml culture fluid was employed.

Figure 9:
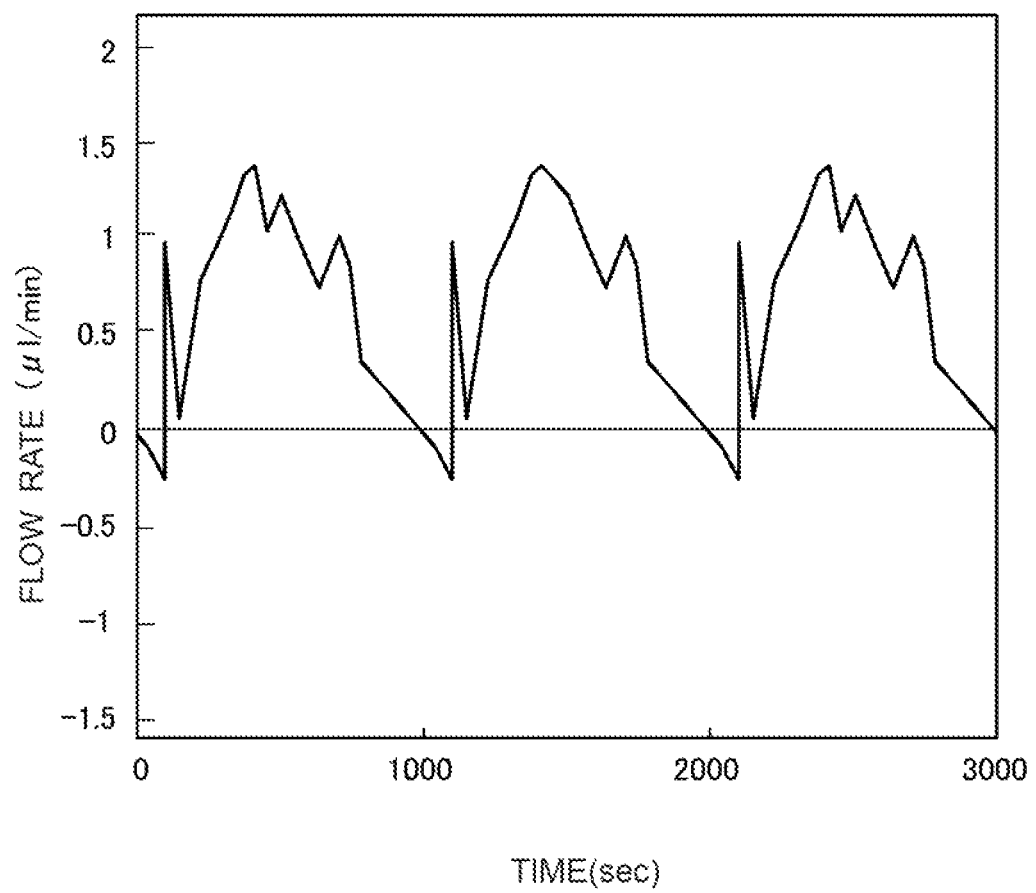
FIG. 9 is a graph illustrating a relationship between elapsed time and culture fluid flow rate in a cell culture device of a comparative example, to which neither a pressure equalizing mechanism, nor a pressurizing mechanism, are provided.
Figure 10:
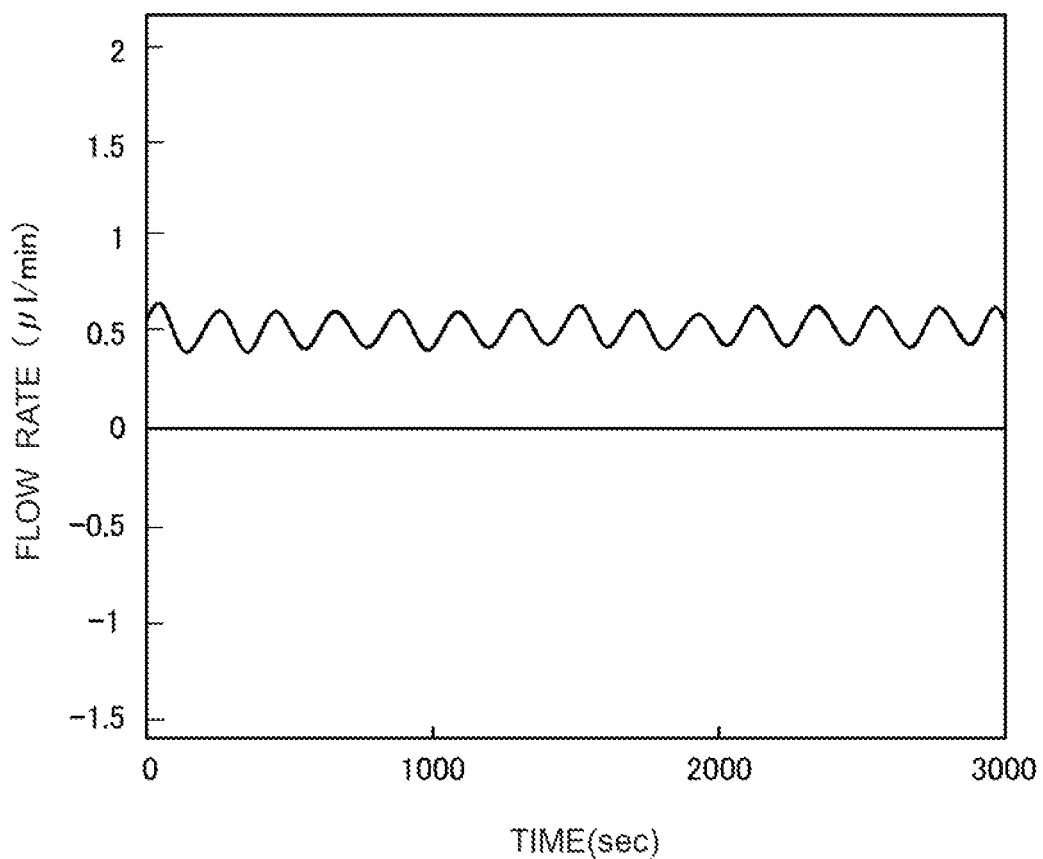
FIG. 10 is a graph illustrating a relationship between elapsed time and culture fluid flow rate in the cell culture device according to the first exemplary embodiment.

It can be seen from the test results, as illustrated in FIG. 9, that in the cell culture device of the Comparative Example, the pulsations of circulation pumps 16 are reflected unmodified in the flow rate, and the flow rate periodically fluctuated in a range of from −0.2 μl/min to 1.3 μl/min. Cells can sustain damage when such large fluctuations are present in the flow rate. As illustrated in Table 1, in the cell culture device of the Comparative Example that is not provided with the pressure equalizing mechanism 18 and the pressurization mechanism 22, all the cells were dead by the third day.

In contrast, as illustrated in FIG. 10, in the cell culture device 10 according to the present exemplary embodiment in which the pressure equalizing mechanisms 18 and the pressurization mechanisms 22 are connected, the pulsations are suppressed, and it can be confirmed that the culture fluid flow rate was stable at around 0.5 μl/min, demonstrating that the cell culture device 10 enables cell culture to be performed in a stable environment.

As illustrated in Table 1, in the cell culture device 10 according to the present exemplary embodiment, there was no occurrence of all the cells dying up to at least the third day. Moreover, in the cell culture device 10 according to the present exemplary embodiment, for all the flow rates set, the flow rate (measured values) fluctuation range was small, at 20% or less of the set values. Namely, the cell culture device 10 according to the present exemplary embodiment can be said to have a high resolution capability with regards to flow rate control, and setting values can be finely controlled by changing the set flow rate. For example, when seeking an appropriate flow rate for culture of the cells, the flow rate can be finely set and the determination precision of the most appropriate value can be increased by using the cell culture device 10 according to the present exemplary embodiment. Using the example illustrated in Table 1, at the set flow rates of 0.3 μl/min, 0.5 μl/min and 0.75 μl/min, there is no duplication of measured values, thereby enabling the effect at each rate set to be precisely compared and evaluated. Note that in the present example, it can be seen that a high cell survival rate can be achieved when the culture fluid flow rate is 0.5 μl/min. Note that the quantity ratio exceeds 100% owing to the fact that the cells have divided. When culturing cells, for example, finer adjustment is possible with respect to the set flow rate for cell cultivation, enabling culture under the most appropriate laminar flow conditions.

The one aspect of the present invention enables the flow rate (measured values) fluctuation range to be suppressed to within a range of from 0% to 50% of a set value. For example, the cell culture device 10 according to the present exemplary embodiment enables the flow rate (measured values) fluctuation range to be suppressed to within 3% to 30% of a set value.

TABLE 1

| Flow rate (μl/min) | Pressure equalizing mechanism and pressurizing mechanism present? | First day (Cell No.) | Third day (Cell No.) | Cell No. ratio (%) of third day to first day |
| --- | --- | --- | --- | --- |
| 0.5 | No | 13.5 | 0 | 0 |
| 0.3 | Yes | 328 | 101 | 31 |
| 0.5 | Yes | 335 | 397 | 119 |
| 0.75 | Yes | 40 | 1 | 3 |

Second Exemplary Embodiment

Explanation follows regarding a cell culture device 70 according to a second exemplary embodiment of the present invention. Note that the same reference numerals are applied for configurations that are the same as in the first exemplary embodiment, and explanation thereof is omitted.

Figure 11:
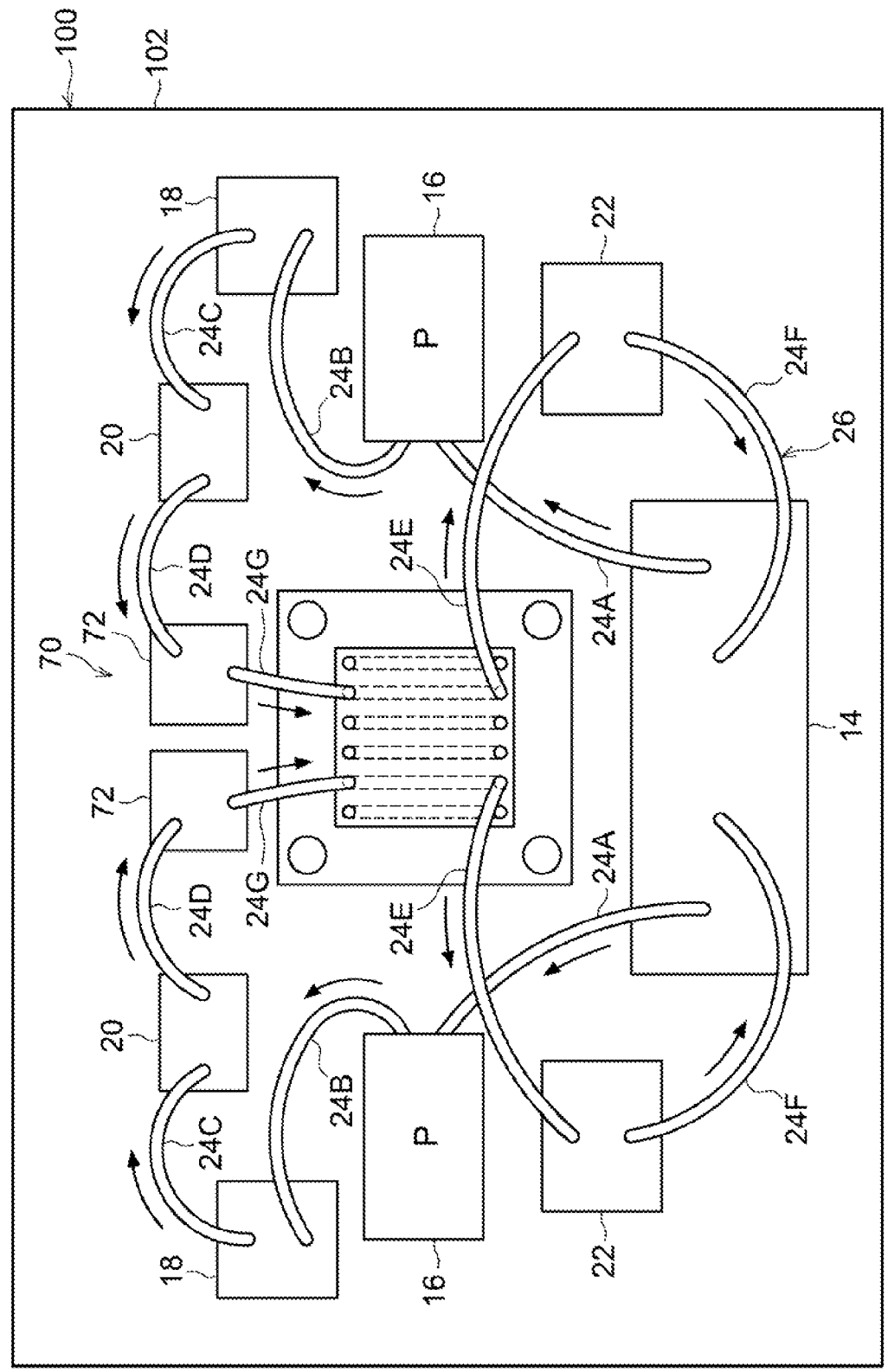
FIG. 11 is a plan view illustrating an overall configuration of a cell culture device according to a second exemplary embodiment.

As illustrated in FIG. 11, the cell culture device 70 according to the present exemplary embodiment is housed in an incubator 102 and maintained at 37 degrees C., similarly to the first exemplary embodiment. Moreover, the cell culture device 70 is provided with a cell culture section 12, a reservoir 14, circulation pumps 16, pressure equalizing mechanisms 18, air traps 20 and pressurization mechanisms 22. Furthermore, second pressure equalizing mechanisms 72 are disposed between the air traps 20 and a culture chamber 12B. The second pressure equalizing mechanisms 72 are connected to the cell culture section 12 by tubes 24G.

The second pressure equalizing mechanisms 72 have a similar construction to the first pressure equalizing mechanisms 18, and are configured so as to be capable of suppressing pressure fluctuations. Note that in the present exemplary embodiment, the second pressure equalizing mechanisms 72 are, as an example, provided between the air traps 20 and the cell culture section 12, however configuration is not limited thereto, and the second pressure equalizing mechanisms 72 may be connected to other sections, for example between the pressure equalizing mechanisms 18 and the air traps 20.

In the cell culture device 70 according to the present exemplary embodiment, culture fluid flows through the pressure equalizing mechanisms 18 and the second pressure equalizing mechanisms 72, thereby enabling greater suppression of pulsations compared to in the first exemplary embodiment, in which only the pressure equalizing mechanisms 18 are provided.

Figure 12:
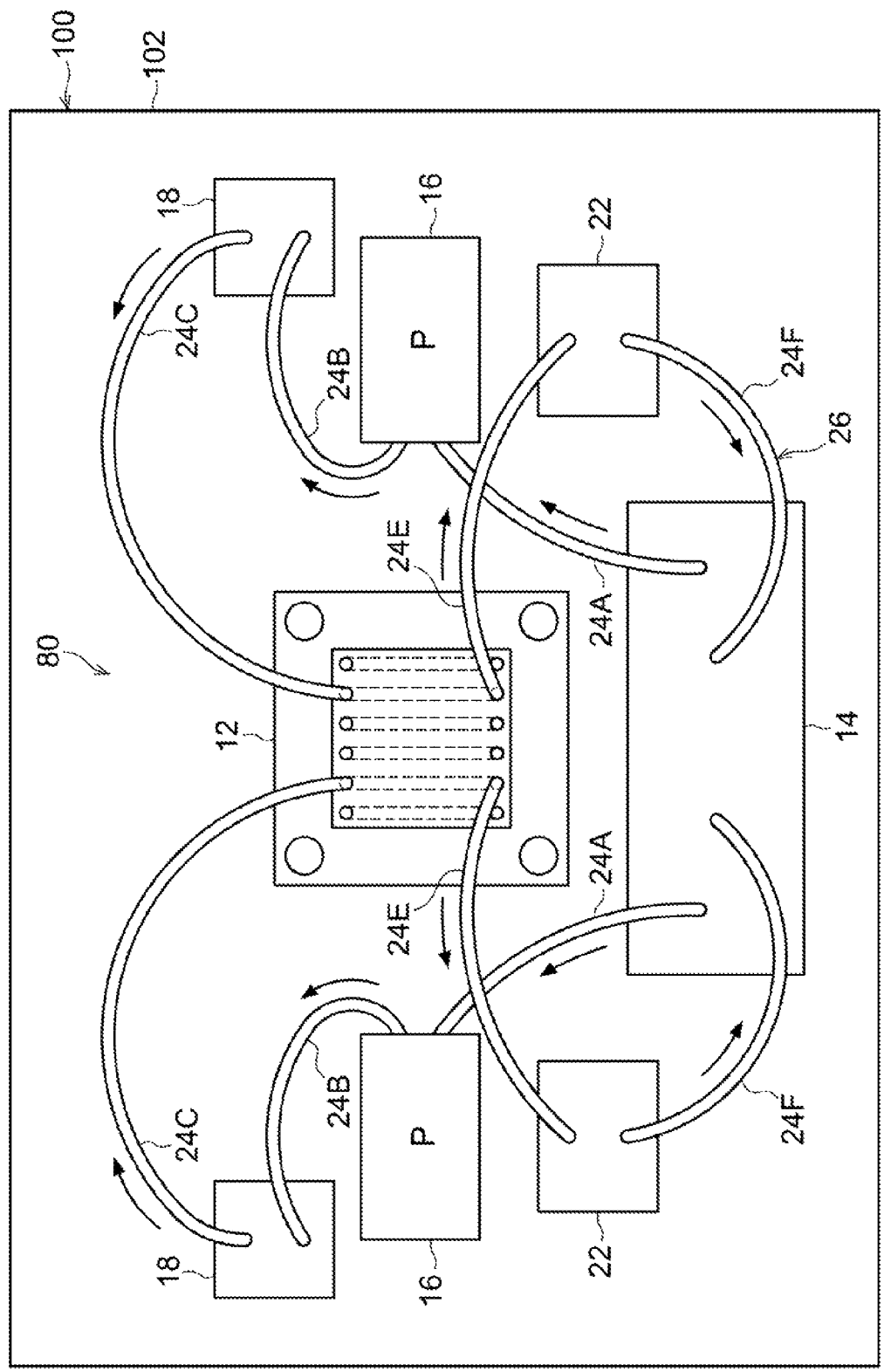
FIG. 12 is a plan view illustrating a first modified example of a cell culture device.

The first exemplary embodiment and the second exemplary embodiment of the present invention have been explained above, however the present invention is not limited by these exemplary embodiments; a combination of the embodiments may be employed, and it goes without saying that various other embodiments may be implemented within a range not departing from the spirit of the present invention. For example, as illustrated in FIG. 12, a cell culture device 80 without an air trap may also be employed.

Figure 13:
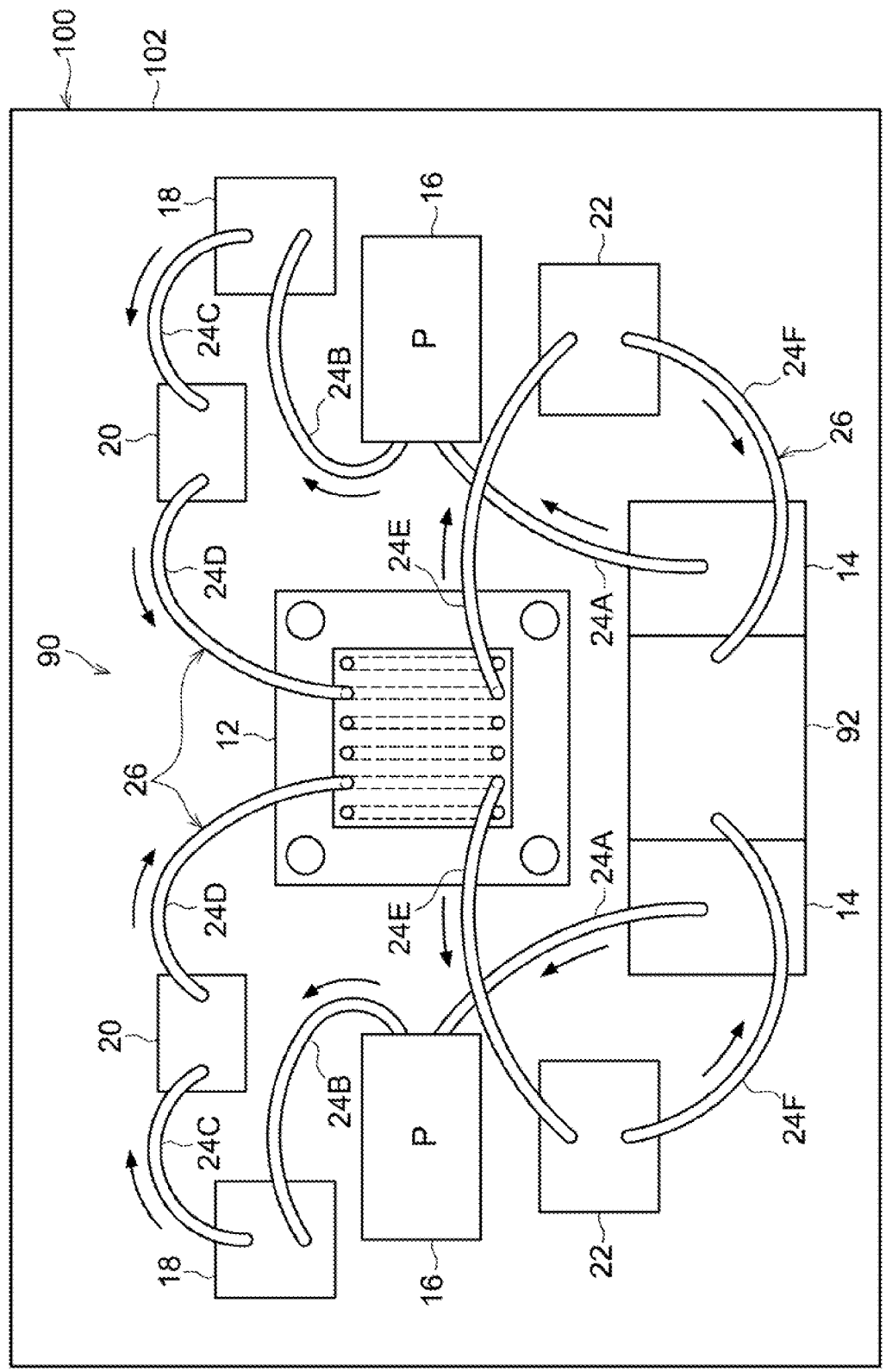
FIG. 13 is a plan view illustrating a second modified example of a cell culture device.

Moreover, as illustrated in FIG. 13, a cell culture device 90 in which culture fluid is delivered from reservoirs 14 in one direction without circulating in a flow path may also be employed. In this case, culture fluid delivered from reservoirs 14 to a cell culture section 12 is discharged into a waste fluid tank 92 through pressurization mechanisms 22.

The invention claimed is:

1. A cell culture device comprising:
    a cell culture section that cultures cells;
    a storage section that stores a culture fluid;
    a flow path that connects the cell culture section and the storage section;
    a fluid delivery device that is provided at the flow path and that delivers the culture fluid from the storage section to the cell culture section;
    a pressure equalizing unit that is provided at the flow path and that suppresses fluctuations in pressure imparted to the culture fluid delivered to the cell culture section; and
    a pressurization unit that is provided at the flow path at a flow outlet side of the cell culture section and that applies a specific pressure to the culture fluid, wherein the pressurization unit comprises:
- a pressurization portion that is connected to the flow path, and that has a smaller cross-sectional area than the flow path; and
- a diaphragm that configures a portion of a wall face of the pressurization portion, and that undergoes resilient outward deformation to widen the flow path, due to pressure of the culture fluid that has flowed into the pressurization portion;

a fluid chamber charged with the culture fluid comprises
- a flow inlet and a flow outlet that are formed at the fluid chamber and are connected to the flow path; and
- a flexible membrane that configures a portion of an inner wall of the fluid chamber, and that flexes outward or inward according to pressure fluctuations in the fluid chamber.

2. The cell culture device of claim 1, wherein:
the flow inlet and the flow outlet are formed at opposing end portions of the fluid chamber; and
the fluid chamber is formed so as to gradually widen on progression from the end portions toward a center portion.

3. The cell culture device of claim 2, wherein the fluid chamber has a rhombus shape with rounded corners in plan view.

4. The cell culture device of claim 1, wherein a gas bubble removal part that removes gas bubbles is provided at the flow path at a flow inlet side of the cell culture section.

5. The cell culture device of claim 1, comprising a plurality of the pressure equalizing unit.

6. A cell culture system comprising:
the cell culture device of claim 1; and
a thermostatic container that houses the cell culture device.

7. A method to culture cell that employs the cell culture device of claim 1 to culture cells, wherein the method comprises:
- a step of adding cells to at least one of the cell culture section, the storage section, or the pressure equalizing unit of the cell culture device; and
- a step of circulating the culture fluid within the flow path using the fluid delivery device while pressurizing the culture fluid within the flow path using the pressurization unit.

* * * * *